United States Patent [19]

Wu et al.

[11] Patent Number: 5,689,026
[45] Date of Patent: Nov. 18, 1997

[54] HYDRODEALKYLATION PROCESS

[75] Inventors: An-hsiang Wu, Bartlesville; Charles A. Drake, Nowata; Ralph J. Melton, Bartlesville, all of Okla.

[73] Assignee: Phillips Petroleum Company, Bartlesville, Okla.

[21] Appl. No.: 637,118

[22] Filed: Apr. 24, 1996

[51] Int. Cl.$^6$ .............................. C07C 5/22; C07C 4/12; C07C 2/52

[52] U.S. Cl. .................... 585/475; 585/489; 585/483; 585/418

[58] Field of Search ................... 585/489, 483, 585/456, 498

[56] References Cited

U.S. PATENT DOCUMENTS

| | | | |
|---|---|---|---|
| 4,568,655 | 2/1986 | Olek et al. | 502/66 |
| 4,835,336 | 5/1989 | McCullen | 585/419 |
| 5,030,787 | 7/1991 | Absil et al. | 585/475 |
| 5,135,643 | 8/1992 | Ward | 208/137 |
| 5,166,111 | 11/1992 | Zones et al. | 502/64 |
| 5,396,010 | 3/1995 | Harandi et al. | 585/418 |
| 5,399,258 | 3/1995 | Fletcher et al. | 208/89 |

*Primary Examiner*—Glenn A. Caldarola
*Assistant Examiner*—Tanaga Anne Booger
*Attorney, Agent, or Firm*—Karl K. Brandes; Lucas K. Shay

[57] ABSTRACT

A process for hydrodealkylating $C_9$–$C_{12}$ alkyl-substituted benzenes (preferably trimethylbenzenes) to $C_6$–$C_8$ aromatic hydrocarbons (in particular, toluene and xylenes) and $C_1$–$C_5$ alkanes employs a catalyst containing zeolite Beta, nickel, molybdenum and sulfur (preferably as sulfides of nickel and of molybdenum).

20 Claims, No Drawings

HYDRODEALKYLATION PROCESS

BACKGROUND OF THE INVENTION

This invention relates to the zeolite-catalyzed hydrodealkylation of $C_9+$ aromatic hydrocarbons to $C_6$–$C_8$ aromatic hydrocarbon and light alkanes.

Recent efforts to convert gasoline to more valuable petrochemical products have focused on the conversion of gasoline to aromatic hydrocarbons by catalytic cracking in the presence of zeolite catalysts. The thus-produced aromatics include BTX (benzene, toluene and xylenes), which are useful feedstocks for producing various organic compounds and polymers, but also heavier, less useful aromatics. It is an object of this invention to convert these higher aromatics (mainly trimethyl- and tetramethylbenzenes) to the more valuable BTX hydrocarbons by catalytic hydrodealkylation. A promoted zeolite catalyst is employed in the process of this invention. This catalyst exhibits high $C_9+$ aromatics conversion activity, good selectivity to xylenes (the presently most valuable BTX hydrocarbons), and little deactivation (caused by coking and feed poisons).

SUMMARY OF THE INVENTION

It is an object of this invention to convert $C_9+$ aromatic hydrocarbons to $C_6$–$C_8$ aromatic hydrocarbons at a high yield in the presence of an effective zeolite. It is a particular object of this invention to employ a promoted zeolite Beta catalyst which exhibits high hydrodealkylation activity, satisfactory selectivity to xylenes, and good stability. Other objects and advantages will be apparent from the detailed description and the appended claims.

In accordance with this invention, a hydrodealkylation process comprises contacting (a) a fluid feed which comprises (preferably consists essentially of) at least one alkyl-substituted benzene containing 9 to 12 carbon atoms per molecule and (b) hydrogen gas with (c) a catalyst which comprises (i) zeolite Beta, (ii) nickel, (iii) molybdenum and (iv) sulfur, at effective hydrodealkylation conditions so as to convert said at least one alkyl-substituted benzene to a product comprising ($\alpha$) at least one aromatic product hydrocarbon containing 6 to 8 carbon atoms per molecule and ($\beta$) at least one alkane containing 1 to 5 carbon atoms per molecule. The presently preferred alkyl-substituted benzenes contained in the feed are tri- and tetramethylbenzenes, in particular 1,2,4-trimethylbenzene (pseudocumene).

DETAILED DESCRIPTION OF THE INVENTION

Any aromatics fluid which contains $C_9$–$C_{12}$ alkyl-substituted benzenes can be used as the feed for the process of this invention. The origin of this feed is not critical. However, a preferred feed is a $C_9+$ heavies fraction of a product from a paraffin (in particular gasoline) aromatization reaction. Generally, this heavies fraction contains primarily trimethylbenzenes (such as 1,2,3-trimethylbenzene, 1,2,4-trimethylbenzene, and 1,3,5-trimethylbenzene) and tetramethylbenzenes (such as 1,2,3,4-tetramethylbenzene, 1,2,3,5-tetramethylbenzene and 1,2,4,5-tetramethylbenzene). Additionally, n-propylbenzene, 3-ethyltoluene, 4-ethyltoluene, 3-n-propyltoluene, 4-n-propyltoluene, and 1,3-diethylbenzene can also be present in the feed. Benzene, toluene, ethylbenzene and xylenes are essentially absent from the feed (i.e., the amount of each of these aromatic hydrocarbons is less than about 0.1 weight-%). Thus, no significant alkylation of these lower aromatics by the $C_9+$ aromatic feed hydrocarbons (i.e., no significant transalkylation) occurs as a side-reaction in the hydrodealkylation process of this invention.

Any gas which comprises molecular hydrogen ($H_2$) can be used as component (b) in the process of this invention. This gas can contain about 10–100 volume-% $H_2$. If the $H_2$ content is less than 100%, the remainder of the gas may be any inert gas (such as $N_2$, He, Ne, Ar) or any other gas which does not significantly affect the reaction or the catalyst used therein.

The catalyst employed in the process of this invention containing zeolite Beta (described in U.S. Pat. No. 3,308,069; preferably having a $SiO_2$:$Al_2O_3$ molar ratio of about 5:1 to about 50:1), including zeolite Beta which contains boron (described in U.S. Pat. No. 5,166,111) and/or other metals (such as Ga, In, Zn, Cr, Ge, Sn), (b) nickel (as Ni metal or at least one nickel compound or mixtures thereof), (c) molybdenum (as Mo metal or at least one molybdenum compound or mixtures thereof), and (d) sulfur (as sulfide). Suitable nickel and molybdenum compounds include (but are not limited to) oxides, sulfides, carboxylates, halides, nitrates, sulfates, phosphates, phosphites and the like. The sulfur component (d) of the catalyst is generally chemically combined with nickel, or with molybdenum, or with both metals, generally in the form of sulfides of Ni and/or of Mo.

Preferably, the catalyst also comprises (e) at least one inorganic binder, such as alumina, silica, alumina-silica, aluminum phosphate, clay (e.g., bentonite), and the like, preferably alumina. The catalyst generally comprises (a) about 50–95 weight-% zeolite Beta, (b) about 0.1–10 (preferably about 0.5–5) weight-% nickel (on an elemental basis), (c) about 0.5–20 (preferably about 1–10) weight-% molybdenum (on an elemental basis), (d) about 0.1–10 (preferably about 0.5–5) weight-% sulfur (on an elemental basis) and (e) about 0–50 (preferably about 1–40) weight-% binder. Preferably, the atomic ratio of Mo to Ni is about 1:1 to about 3:1.

The catalyst can be prepared by any suitable, effective means. Preferably, a zeolite Beta material, which generally has been compounded with a binder (described above) and has been shaped (such as pelletized or extruded or tableted), is first impregnated (generally by the incipient wetness method) with a solution (preferably aqueous) containing at least one dissolved nickel compound (preferably nickel nitrate) and at least one dissolved molybdenum compound (preferably ammonium molybdate). The concentrations of the Ni and Mo compounds in the impregnating solution and the weight ratio of this solution to the zeolite Beta material are chosen such as to provide a finished, impregnated catalyst which contains the desired contents of Ni and Mo (recited above). It is within the scope of this invention (yet less preferred) to apply sequential impregnation (in any order) with Ni and Mo compounds, which are contained in separate solutions.

After the impregnation with Ni and Mo compounds has been completed, the Ni/Mo-impregnated zeolite Beta material is calcined (generally in air at a temperature of about 500°–650° C., for about 0.5–20 hours) and then sulfided, i.e., treated with a sulfiding agent (preferably a mixture of about 1–99 mole-% molecular hydrogen and about 99–1 mole-% of at least one sulfur compound such as ammonium sulfide, $CS_2$, COS, $H_2S$, thiophene, alkyl mercaptans, alkyl sulfides, mercaptoalcohols, and mixtures thereof) at a temperature of about 350°–500° C., for about 0.1–5 hours. Alternatively, the calcined Ni/Mo-impregnated zeolite Beta material is first treated with a reducing gas (preferably molecular hydrogen, at a temperature of about 350°–500° C., for about 0.2–10 hours), then treated with a solution (preferably aqueous) of at least one sulfide (such as $H_2S$, ammonium sulfide, alkali metal sulfides, organic sulfides, and mixtures thereof; preferably ammonium sulfide), and finally heated in an inert gas atmosphere (such as $N_2$, He, Ar) at a temperature of about 500°–650° C., for about 0.5–20 hours. Preferably, the concentration of the sulfide in this solution is about 0.1–5 mole/l.

The hydrocarbon feed and hydrogen gas can be contacted with the above-described catalyst in any technically suitable manner at effective hydrodealkylation reaction conditions. Generally, the hydrocarbon feed (which can be liquid or gaseous, preferably being in the vaporized state) and hydrogen gas are passed either through fixed catalyst bed, or a moving catalyst bed, or a fluidized catalyst bed.

Effective hydrodealkylation conditions include a liquid hourly space velocity (LHSV) of the hydrocarbon feed stream in the range of about 0.1 to about 10 $ft^3$ feed/$ft^3$ catalyst/hour. The hydrogen gas hourly space velocity generally is in the range of about 10 to about 100 $ft^3$ $H_2$/$ft^3$ catalyst/hour. The preferred molar ratio of $H_2$ to feed hydrocarbons is about 0.5:1 to about 5:1. Generally, the reaction pressure is about 50–750 psig (preferably 200–600 psig), and the reaction temperature is about 250°–750° C. (preferably about 450°–550° C.).

The hydrodealkylation reactor effluent contains (I) a heavies fraction of unconverted $C_9$+ aromatics and other heavy ($C_9$+) aromatics which may have been formed by side-reactions (such as isomerization), (II) light alkanes, mainly methane, ethane, propane, n-butane, isobutane, and minor amounts (about 5 weight-%) of $C_5$ alkanes (isopentane and n-pentane), and (III) BTX aromatic hydrocarbons (benzene, toluene, ortho-xylene, meta-xylene and para-xylene). Generally, the reactor effluent is separated into these principal fractions by fractional distillation. The heavy fraction (I) can be recycled to the hydrodealkylation reactor, the light fraction (II) can be used as fuel gas or as a feed for other reactions (e.g., in a thermal hydrocarbon cracker to produce ethylene and propylene), and the middle fraction (III) can be further separated into individual $C_6$–$C_8$ aromatic hydrocarbon fractions. Alternatively, fraction (III) can undergo one or more than one reaction (before or after separation to individual $C_6$–$C_8$ hydrocarbons) so as to increase the content of the most desired BTX aromatic hydrocarbon. Suitable examples of such subsequent $C_6$–$C_8$ aromatic hydrocarbon conversions are disproportionation of toluene (to form benzene and xylenes) involving transalkylation benzene and xylenes (to form toluene), and isomerization of meta-xylene and/or ortho-xylene to para-xylene.

After the catalyst has been deactivated (by coke deposition or feed poisons) to an extent that the feed conversion and/or the selectivity to the most valuable $C_6$–$C_8$ aromatic product (generally xylenes) have become unsatisfactory, the catalyst can be reactivated, e.g., by calcining in air (to burn off deposited coke and other carbonaceous materials, such as oligomers or polymers), preferably at a temperature of about 400°–650° C., followed by a reducing treatment (preferably with hydrogen gas at a temperature of about 400°–600° C.). The optimal time periods of the calcining and reducing steps depend on the types and amounts of deactivating deposits on the catalyst and on the calcination and reduction temperatures. These optimal time periods can easily be determined by persons possessing ordinary skills in the field of technology pertaining to this invention.

The following examples are presented to further illustrate this invention and are not to be construed as unduly limiting the scope of the present invention.

EXAMPLE I

This example illustrates the preparation of hydrodealkylation catalysts (within and outside the scope of this invention). All catalyst preparations comprised impregnation of a zeolite Beta by incipient wetness at room temperature.

Catalyst A1 (Control) was a Ni/Mo/zeolite Beta material which had been prepared by impregnating 15.0 grams of a Beta zeolite (1/16" extrudates; provided by UOP Inc., Des Plains, Ill. under the product designation "MD-08318-69, DR #3"") with 10.8 grams of an aqueous 15 weight-% solution of $(NH_4)_6Mo_7O_{24}$, drying (for 3 hours in air at 125° C.) and then calcining (for 6 hours in air at 525° C.) the Mo-impregnated zeolite Beta, impregnating 30.37 grams of the calcined, Mo-impregnated zeolite Beta with 18.6 grams of an aqueous 20 weight-% solution of $Ni(NO_3)_2.6H_2O$, followed by drying, calcining (for 6 hours in air at 525° C.) and finally heating the calcined Mo/Ni-impregnated zeolite Beta for 2 hours in hydrogen gas at 425° C. Catalyst A1 contained 2.5 weight-% Ni and 5.3 weight-% Mo. The Mo:Ni atomic ratio in this catalyst was about 1.3:1.

Catalyst A2 (Control) was another Ni/Mo/zeolite Beta, prepared by impregnating 13.5 grams of UOP's zeolite Beta (described above) with 10.8 grams of a solution which had been prepared by dissolving 5.0 grams of $Ni(NO_3)_2.6H_2O$ and 6.0 grams of $(NH_4)_6Mo_7O_{24}.4H_2O$ in 23.0 grams of water, followed by drying, calcining for 6 hours in air at 525° C. and heating the calcined Ni/Mo-impregnated zeolite Beta for 2 hours in hydrogen gas at 425° C. Catalyst A2 contained 2.18 weight-% Ni and 7.05 weight-% Mo. The Mo:Ni atomic ratio in this catalyst was about 2:1.

Catalyst B (Invention) was a sulfided Ni/Mo/zeolite Beta material which had been prepared by treating 7.5 grams of Catalyst A1 for 2 hours in a gaseous mixture of hydrogen and vaporized carbon disulfide (mole ratio of $H_2$ to vaporized $CS_2$: about 20:1) at a temperature of 400° C. The weight percentages of Mo and Ni and the Mo:Ni atomic ratio were about the same as those in Catalyst A1. The sulfur content was not determined.

Catalyst C (Invention) also was a sulfided Ni/Mo/zeolite Beta material, prepared by impregnating 7.0 grams of Catalyst A2 with 4.5 grams of an aqueous 10 weight-% $(NH_4)_2S$ solution, followed by drying and heating for 4 hours in a helium gas stream (flow rate: 50 cc/minute) at 525° C. Catalyst B contained 3.06 weight-% sulfur. The weight percentages of Ni and Mo and the Mo:Ni atomic ratio were about the same as those in Catalyst A2.

EXAMPLE II

This example illustrates the use of the materials described in Example I as catalysts in the hydrodealkylation of $C_9$+ alkylbenzenes, in particular 1,2,4-trimethylbenzene (pseudocumene), to benzene, toluene and xylenes (BTX).

A stainless-steel reactor robe (inner diameter 0.75 inch; length: 20 inches) was filled with a 5 cc bottom layer of Alundum® alumina (inert, low surface area alumina) 10 cc of one of the catalysts, and a 5 cc top layer of Alundum® alumina. The catalyst was pretreated with flowing hydrogen gas (flow rate: 260 cc $H_2$ per minute) at a temperature being raised from room temperature to a final temperature of 450° C. at a rate of 10° C. per minute. Then the liquid feed, which contained $C_9$+ aromatic hydrocarbons, was introduced at a rate of 40 cc/hour, together with hydrogen gas at a rate of 260 cc $H_2$/minute. The liquid hourly space velocity of the feed was about 4 cc feed/cc catalyst/hour (equivalent to a weight hourly space velocity of about 5.5–6 g feed/g catalyst/hour). The reaction pressure was 500 psig. The reactor effluent was cooled and separated into a gaseous phase and a liquid phase. Both phases were analyzed by gas chromatographs at intervals of about 1 hour.

The liquid feed in two hydrodealkylation runs was a heavy $C_9$+ aromatic hydrocarbon mixture (labeled Feed I) obtained in a gasoline aromatization test. The composition of Feed I is given in Table I; the sulfur content in this feed was less than 2 ppm S. The feed in two other hydrodealkylation runs was 1,2,4-trimethylbenzene (labeled Feed II). Pertinent hydrodealkylation test results are summarized in Table II.

TABLE I

Composition of Feed I

| Feed Component | Weight Percentage |
|---|---|
| Lights ($C_1$–$C_6$) | 0 |
| Benzene, Toluene, Xylenes | 0 |
| n-Propylbenzene | 3.33 |
| 3-Ethyltoluene | 1.52 |
| 4-Ethyltoluene | 2.96 |
| 1,3,5-Trimethylbenzene | 2.15 |
| 1,2,4-Trimethylbenzene | 13.57 |
| 1,2,3-Trimethylbenzene | 3.85 |
| 2,3-Dihydroindene | 2.87 |
| 1,3-Diethylbenzene | 1.87 |
| 3-n-Propyltoluene | 3.19 |
| 4-n-Propyltoluene | 1.13 |
| 1,3-Dimethyl-5-ethylbenzene | 2.13 |
| 1,4-Dimethyl-2-ethylbenzene | 1.87 |
| 1,3-Dimethyl-4-ethylbenzene | 1.16 |
| 1,2-Dimethyl-4-ethylbenzene | 4.54 |
| 1,2,3,4-Tetramethylbenzene | 2.16 |
| 1,2,3,5-Tetramethylbenzene | 2.89 |
| 1,2,4,5-Tetramethylbenzene | 3.38 |
| Naphthalene | 5.12 |

TABLE II

Composition (Wt %) of Reactor Effluent (after about 5 Hours on Stream)

| Run | Feed | Catalyst | $C_9$+ Aromatics | Xylenes | Toluene | Benzene | Lights[1] |
|---|---|---|---|---|---|---|---|
| 1 (Control) | I | A1 (Ni/Mo/Zeolite Beta) | 45.8 | 29.3 | 10.0 | 1.7 | 13.2 |
| 2 (Invention) | I | B (Ni/Mo/S/Zeolite Beta) | 39.0 | 32.9 | 11.0 | 0.9 | 16.3 |
| 3 (Control) | II | A2 (Ni/Mo/Zeolite Beta) | 51.8 | 26.7 | 7.0 | 1.2 | 13.3 |
| 4 (Invention) | II | C (Ni/Mo/S/Zeolite Beta) | 45.7 | 29.6 | 9.8 | 0.9 | 14.0 |

[1]Comprising about 40 weight % methane, about 10 weight % ethane, about 25 weight % propane, about 20 weight % butanes, and about 5 weight % pentanes.

Test results in Table 2 clearly demonstrate the following advantages of invention runs 2 and 4, respectively (employing Ni/Mo/S/zeolite Beta catalysts) over corresponding control runs 1 and 3, respectively (employing catalysts without sulfur): (1) lower content of $C_9$+ aromatic hydrocarbons in the reactor effluent, i.e., higher conversion of the feed to BTX; (2) higher yield of xylenes (the most valuable lower aromatics), and (3) higher toluene yield.

Reasonable variations, modifications and adaptations for various usages and conditions can be made within the scope of the disclosure and the appended claims, without departing from the scope of this invention.

That which is claimed is:

1. A hydrodealkylation process comprising contacting (a) a fluid feed which comprises at least one alkyl-substituted benzene containing 9 to 12 carbon per molecule atoms and (b) hydrogen with (c) a catalyst comprising (I) zeolite Beta, (ii) nickel, (iii) molybdenum and (iv) sulfur, at effective hydrodealkylation conditions so as to convert said at least one alkyl-substituted benzene to a product comprising (α) at least one aromatic product hydrocarbon containing 6 to 8 carbon atoms per molecule and (β) at least one alkane containing 1 to 5 carbon atoms per molecule wherein:

said catalyst is prepared by the steps comprising: (1) impregnating a zeolite Beta material with compounds of nickel and molybdenum to produce a nickel- and molybdenum-impregnated zeolite Beta material; (2) calcining Said nickel- and molybdenum-impregnated zeolite Beta material to produce a calcined nickel- and molybdenum-impregnated zeolite Beta material; and (3) sulfiding said calcined nickel- and molybdenum-impregnated zeolite Beta material, said sulfiding is selected from the group consisting of (A) treating said calcined nickel- and molybdenum-impregnated zeolite Beta material with a mixture of about 1–99 mole-% hydrogen gas and about 99–1 mole-% of at least one sulfur compound selected from the group consisting of ammonium sulfide, carbon disulfide, carbonyl sulfide, hydrogen sulfide, thiophene, alkyl mercaptans, alkyl sulfides and mercaptoalcohols at a temperature of about 350°–500° C.

(B) reducing said calcined nickel- and molybdenum-impregnated Beta material, and thereafter treating said material with a solution of at least one sulfide selected from the group consisting of hydrogen sulfide, ammonium sulfide and alkali metal sulfides, and (C) combinations thereof.

2. A process in accordance with claim 1, wherein benzene, toluene, ethylbenzene and xylenes are essentially absent from said fluid feed.

3. A process in accordance with claim 2, wherein said catalyst comprises about 50–95 weight-% zeolite Beta, about 0.1–10 weight-% nickel, about 0.5–20 weight-% molybdenum and about 0.1–10 weight-% sulfur.

4. A process in accordance with claim 3, wherein components (ii), (iii) and (iv) are chemically combined as sulfides of nickel and molybdenum.

5. A process in accordance with claim 4, wherein said catalyst comprises about 0.5–5 weight-% nickel, about 1–10 weight-% molybdenum and about 0.5–5 weight-% sulfur.

6. A process in accordance with claim 3, wherein said catalyst additionally comprises at least one inorganic binder.

7. A process in accordance with claim 6, wherein said at least one inorganic binder is selected from the group consisting of alumina, silica, alumina-silica, aluminum phosphate and clay.

8. A process in accordance with claim 7, wherein said at least one inorganic binder is present in said catalyst at a level of about 1–40 weight-%.

9. A process in accordance with claim 8, wherein said catalyst comprises about 0.5–5 weight-% nickel, about 1–10 weight-% molybdenum, about 0.5–5 weight-% sulfur, and about 1–40 weight-% inorganic binder.

10. A process in accordance with claim 2, wherein said effective hydrodealkylation conditions comprise a liquid hourly space velocity of said fluid feed in the range of about 0.1 ft$^3$/ft$^3$ catalyst/hour to about 10 ft$^3$/ft$^3$ catalyst/hour, a gas hourly space velocity of said hydrogen gas in the range of about 10 ft$^3$/ft$^3$ catalyst/hour to about 100 ft$^3$/ft$^3$ catalyst/hour, a molar ratio of hydrogen to feed hydrocarbons in the range of about 0.5:1 to about 5:1, a reaction pressure in the range of about 50 psig to about 750 psig, and a reaction temperature in the range of about 250° C. to about 750° C.

11. A process in accordance with claim 10, wherein said effective hydrodealkylation conditions comprise a reaction pressure of about 200–600 psig and a reaction temperature of about 450°–550° C.

12. A process in accordance with claim 1, wherein said at least one alkyl-substituted benzene contained in said fluid feed is selected from the group consisting of 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, and 1,3-diethylbenzene.

13. A process in accordance with claim 2, wherein said at least one alkyl-substituted benzene contained in said fluid feed is selected from the group consisting of 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, and 1,3-diethylbenzene.

14. A process in accordance with claim 13, wherein said at least one alkyl-substituted benzene is 1,2,4-trimethylbenzene.

15. A process in accordance with claim 1, wherein said sulfiding comprises treating said calcined nickel- and molybdenum-impregnated zeolite Beta material with a mixture of about 1–99 mole-% hydrogen gas and about 99–1 mole-% of at least one ammonium sulfide sulfur compound selected from the group consisting of ammonium sulfide carbon disulfide, carbonyl sulfide, hydrogen sulfide, thiophene, alkyl mercaptans, alkyl sulfides and mercaptoalcohols at a temperature of about 350°–500° C. for a time period of about 0.1–5 hours.

16. A process in accordance with claim 1, wherein said sulfiding comprises reducing said calcined nickel- and molybdenum-impregnated Beta material, and thereafter treating said material with a solution of at least one sulfide selected from the group consisting of hydrogen sulfide, ammonium sulfide and alkali metal sulfides.

17. A hydrodealkylation process comprising contacting a fluid feed with hydrogen gas in the presence of a catalyst under a sufficient reaction condition to effect the production of an aromatic hydrocarbon containing 6 to 8 carbon atoms per molecule wherein:

said fluid feed comprises a $C_9$+ aromatic hydrocarbon;

said catalyst comprises about 50 to about 95 weight % zeolite Beta, about 0.1 to about 10 weight % nickel, about 0.5 to about 20 weight % molybdenum, and about 0.1 to about 10 weight % sulfur;

said catalyst is prepared by the steps comprising; (1) impregnating a zeolite Beta material with compounds of nickel and molybdenum to produce a nickel- and molybdenum-impregnated zeolite Beta material; (2) calcining said nickel- and molybdenum-impregnated zeolite Beta material; and (3) treating said calcined, nickel- and molybdenum-impregnated zeolite Beta material with a sulfur-containing fluid comprising about 1 to about 99 mole % hydrogen and about 1 to about 99 mole % of a sulfur compound selected from the group consisting of carbon disulfide, carbonyl sulfide, hydrogen sulfide, thiophene, alkyl mercaptans, alkyl sulfides, ammonium sulfide, mercaptoalcohols, and combinations of any two or more thereof, at a temperature of about 300°–500° C.; and said reaction condition comprises a liquid hourly space velocity of said fluid feed in the range of about 0.1 ft$^3$/ft$^3$ catalyst/hour to about 10 ft$^3$/ft$^3$ catalyst/hour, a gas hourly space velocity of said hydrogen in the range of about 10 ft$^3$/ft$^3$ catalyst/hour to about 100 ft$^3$/ft$^3$ catalyst/hour, a molar ratio of hydrogen to said fluid feed in the range of about 0.5:1 to about 5:1, a reaction pressure in the range of about 50 psig to about 750 psig, and a reaction temperature in the range of about 250° C. to about 750° C.

18. A process in accordance with claim 17 wherein:

a $C_6$–$C_8$ aromatic hydrocarbon is essentially absent from said fluid feed;

said catalyst comprises about 0.5 to about 5 weight % nickel, about 1 to about 10 weight % molybdenum and about 0.5 to about 5 weight % sulfur;

said treating of said calcined nickel- and molybdenum-impregnated zeolite Beta material with said sulfur containing fluid is carried out for a time period of about 0.1–5 hours;

said sulfur compound is carbon disulfide; and said reaction pressure is in the range of from about 200 to about 600 psig and said reaction temperature is in the range of from about 450° C. to about 550° C.

19. A hydrodealkylation process comprising contacting a fluid feed with hydrogen gas in the presence of a catalyst under a sufficient reaction condition to effect the production of an aromatic hydrocarbon containing 6 to 8 carbon atoms per molecule wherein:

said fluid feed comprises a $C_9$+ aromatic hydrocarbon;

said catalyst comprises about 50 to about 95 weight % zeolite Beta, about 0.1 to about 10 weight % nickel, about 0.5 to about 20 weight % molybdenum, and about 0.1 to about 10 weight % sulfur;

the preparation of said catalyst comprises the steps of: (1) impregnating a zeolite Beta material with compounds of nickel and molybdenum to produce a nickel- and molybdenum-impregnated zeolite Beta material; (2) calcining said nickel- and molybdenum-impregnated zeolite Beta material to produce a calcined, nickel-and molybdenum-impregnated zeolite Beta material, (3) reducing said calcined, nickel- and molybdenum-impregnated zeolite Beta material, and thereafter (4) treating said calcined, nickel- and molybdenum-impregnated zeolite Beta material with a solution of a sulfide selected from the group consisting of hydrogen sulfide, ammonium sulfide, alkali metal sulfides, and combinations of any two or more thereof; and said reaction condition comprises a liquid hourly space velocity of said fluid in the range of about 0.1 ft$^3$/ft$^3$ catalyst/hour to about 10 ft$^3$/ft$^3$ catalyst/hour, a gas hourly space velocity of said hydrogen in the range of about 10 ft$^3$/ft$^3$ catalyst/hour to about 100 ft$^3$/ft$^3$ catalyst/hour, a molar ratio of hydrogen to said fluid in the range of about 0.5:1 to about 5:1, a reaction pressure in the range of about 50 psig to about 750 psig, and a reaction temperature in the range of about 250° C. to about 750° C.

20. A process in accordance with claim 19 wherein:

a $C_6$–$C_8$ aromatic hydrocarbon is essentially absent from said fluid;

said catalyst comprises about 0.5 to about 5 weight % nickel, about 1 to about 10 weight % molybdenum and about 0.5 to about 5 weight % sulfur;

said at least one sulfide is ammonium sulfide; and said reaction pressure is in the range of from about 200 to about 600 psig and said reaction temperature is in the range of from about 450° C. to about 550° C.

* * * * *

UNITED STATES PATENT AND TRADEMARK OFFICE
CERTIFICATE OF CORRECTION

PATENT NO.   : 5,689,026

DATED        : November 18, 1997

INVENTOR(S)  : An-hsiang Wu et al

It is certified that error appears in the above-identified patent and that said Letters Patent is hereby corrected as shown below:

Column 7, claim 10, line 15, the number "0. 1" should read "0.1".

Column 7, claim 15, line 48, the words "ammonium sulfide" between "one" and "sulfur" should be deleted"

Signed and Sealed this

Third Day of March, 1998

*Attest:*

BRUCE LEHMAN

*Attesting Officer*      *Commissioner of Patents and Trademarks*